United States Patent
Rogers et al.

(10) Patent No.: US 6,878,134 B2
(45) Date of Patent: Apr. 12, 2005

(54) SAFETY NEEDLE ASSEMBLY WITH LOCKING RETRACTION

(75) Inventors: Bob Rogers, San Diego, CA (US); Mark Godfrey, Ramona, CA (US)

(73) Assignee: Aragon Medical, San Diego, CA (US)

( * ) Notice: Subject to any disclaimer, the term of this patent is extended or adjusted under 35 U.S.C. 154(b) by 0 days.

(21) Appl. No.: 10/289,127

(22) Filed: Nov. 4, 2002

(65) Prior Publication Data

US 2004/0087913 A1 May 6, 2004

(51) Int. Cl.[7] .......................... A61M 5/178; A61M 5/00
(52) U.S. Cl. .................. 604/164.01; 604/110; 604/198
(58) Field of Search ........................ 604/110, 164.01, 604/164.08, 164.07, 164.12, 168.01, 192, 198

(56) References Cited

U.S. PATENT DOCUMENTS

| | | | |
|---|---|---|---|
| 4,762,516 A | | 8/1988 | Luther et al. |
| 4,944,725 A | | 7/1990 | McDonald |
| 4,950,252 A | | 8/1990 | Luther et al. |
| 5,053,017 A | | 10/1991 | Chamuel |
| RE34,416 E | * | 10/1993 | Lemieux ..................... 604/164 |
| 5,273,540 A | | 12/1993 | Luther et al. |
| 5,300,045 A | * | 4/1994 | Plassche, Jr. ............... 604/263 |
| 5,688,249 A | | 11/1997 | Chang et al. |
| 5,725,503 A | | 3/1998 | Arnett |
| 5,954,698 A | | 9/1999 | Pike |
| 6,582,402 B1 | * | 6/2003 | Erskine ................. 604/164.08 |
| 2001/0044604 A1 | | 11/2001 | Luther |

* cited by examiner

Primary Examiner—Michael J. Hayes
(74) Attorney, Agent, or Firm—Fish & Richardson P.C.

(57) ABSTRACT

Provided is an assembly in which a needle is safely housed in a cover. A safety mechanism prevents the needle from being removed from a device, unless the needle is in a "needle safe position".

9 Claims, 8 Drawing Sheets

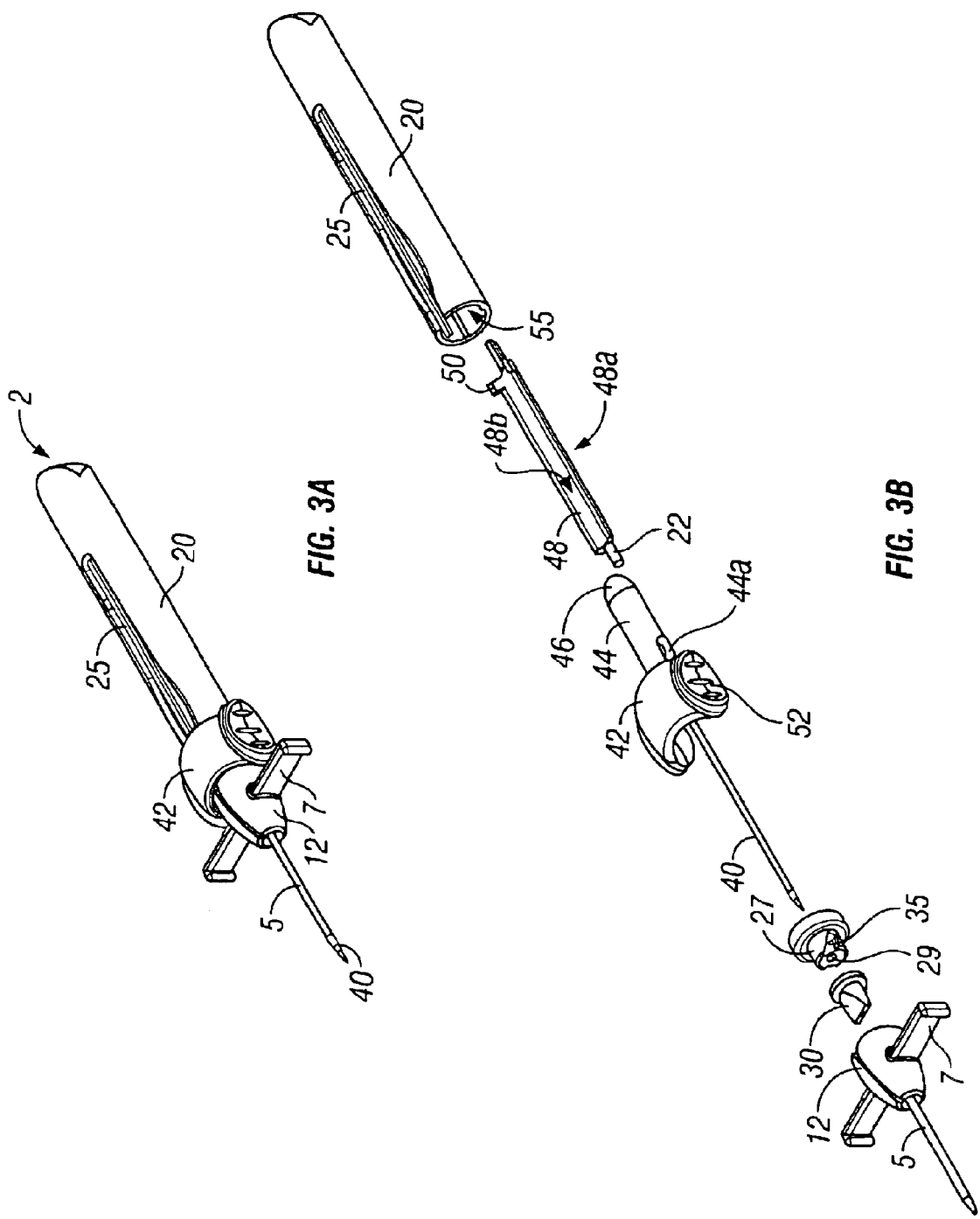

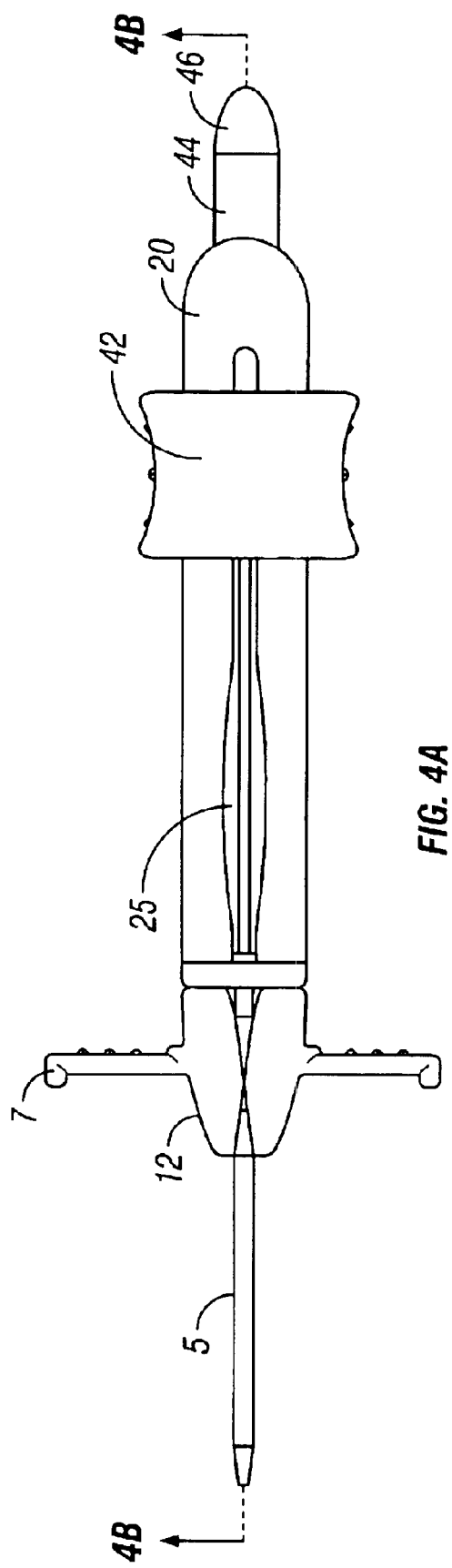
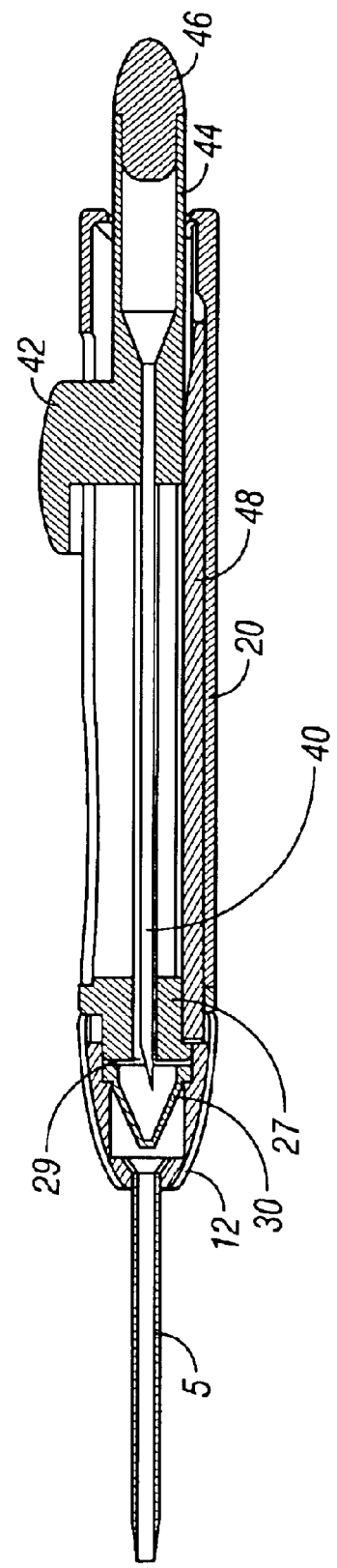
FIG. 4A
FIG. 4B

SAFETY NEEDLE ASSEMBLY WITH LOCKING RETRACTION

BACKGROUND

There are a number of medical, diagnostic, and research procedures that require the use of needles. During use the needles come in contact with pathogens or toxic materials that are harmful to subjects, researchers, and medical practitioners.

For example, many different kinds of medical procedures require that a needle be inserted into a subject thereby coming into contact with the subject's fluids, blood, or other tissues. Such a needle may be present in conjunction with a wide variety of other devices, including, but not limited to, syringes, catheters, and introducers. In the medical field, the needle is typically intended for bodily penetration. Once it comes into contact with the subject's tissues, the needle becomes contaminated and extremely dangerous. A contaminated needle may transmit one or more of many different forms of blood-transmitted diseases, including, for example, the HIV virus, the hepatitis B virus, and the like. Hence, a contaminated needle is dangerous and in fact potentially deadly.

Many different safety techniques have been suggested for dealing with contaminated needles. One safety technique attempts to automatically insert a cover over the needle end when the needle is removed from contact with the patient (see, e.g., U.S. Pat. Nos. 5,053,017; 5,312,345; 5,688,249; and 6,117,108). This system may still allow contact with parts of the needle, which may have blood or tissue on them, even though it may cover the needle end.

Another safety technique allows the needle to be retracted into a housing after removal (see, e.g., U.S. Pat. Nos. 4,747,831; 4,950,252; 5,215,528; and 5,273,540). This system has advantages because the needle is totally encased within the housing when in a safe position. However, the needle may be pulled from the patient without actually being in a safe position. In other words, operator error may lead to an unsafe condition in which a contaminated needle is exposed.

SUMMARY OF THE INVENTION

The invention provides an assembly in which a needle is housed in a cover that automatically covers the needle. A safety mechanism locks the whole mechanism into place and thereby prevents the needle from being removed from a subject, or removed from a device comprising a dangerous material, unless the needle is in a "needle safe position" inside a housing. In this way, the system automatically prevents anyone from removing a tainted needle from a user or device until the needle is in a "needle safe position".

In one embodiment, an operation to remove the needle comprises retracting the needle into a housing using a first sliding part until the needle engages a second sliding part operably connected to a locking mechanism. Further sliding of the first sliding part results in the movement of the second sliding part whereby the locking mechanism is unlocked. This unlocking enables removal of the needle, now in a needle safe position, from its connection mechanism, e.g. a catheter or introducer. The removal from the connection mechanism is carried out by a second sliding operation in which a second part slides to physically move a tab, thus enabling removal.

The invention provides a safety needle assembly, comprising a needle, which is movable between an extended position, and a retracted position having a locking assembly that locks the needle in the retracted position. A mechanical movement assembly allows another movement only when the needle is safely positioned within the housing in a retracted position, the other movement being one that enables removing the needle assembly from a connected device. In one embodiment, the safety needle assembly further comprises a housing, and the needle assembly is movable between the extended position in which it extends outside the housing, and the retracted position in which it retracts inside inner surfaces defining the housing. In another embodiment, the other movement comprises another retraction of another device relative to the housing. The mechanical movement assembly comprises a slide assembly, and the retraction relative to the housing comprises sliding the slide assembly against inner surfaces of the housing.

The invention provides a rotation based connection system for connecting a catheter or introducer to a needle housing. The needle system comprises a hollow needle and a connector portion, fluidly connected to the hollow needle, wherein the connector portion comprises a flash chamber and at least one attachment detent. The system includes a needle housing comprising a first end having an opening and one or more threads; a second end comprising at least one locking detent/ledge, an outer surface; and an inner surface, the inner surface defining a first sliding area. A needle handle, comprising an outer handle portion located on the outer surface of the housing is capable of sliding a substantial length of the needle housing. The needle handle comprises an inner handle portion within the inner surface of the needle housing having a needle that is fluidly connected to the inner handle portion and which is in alignment with the opening on the first end of the housing. A sliding mechanism comprising a first end having a locking tab and a second end comprising a tongue and at least one flange is also included in the system. The sliding mechanism is located within the inner surface of the needle housing between the inner handle portion and the housing. The connector portion of the system is capable of attachment and removal of catheters and introducers from the first end of the housing.

The invention also provides a needle system comprising a friction-based connection. This needle system comprises a hollow needle and a connector portion, fluidly connected to the hollow needle, wherein the connector portion comprises a flash chamber and at least one attachment detent. The system includes a needle housing comprising a first end having an opening and a latching mechanism; a second end comprising at least one locking detent/ledge; an outer surface; and an inner surface, the inner surface defining a first sliding area. A needle handle comprising an outer handle portion located on the outer surface of the housing is capable of sliding a substantial length of the needle housing. The handle comprises an inner handle portion within the inner surface of the needle housing and a needle fluidly connected to the inner handle portion and in alignment with the opening on the first end of the housing. A sliding mechanism having a first end comprising a locking tab, and a second end comprising a tongue and at least one flange is also included in the system. The sliding mechanism is located within the inner surface of the needle housing between the inner handle portion and the housing. The locking tab interacts with a grasping mechanism located on the housing such that the removal of contact of the locking tab, by retraction, removes the interaction between the grasping member and the locking tab thereby allowing removal of the housing from a catheter or introducer comprising the connector portion. Accordingly, the system allows for the attachment and removal of catheters and introducers from the first end of the housing.

BRIEF DESCRIPTION OF THE DRAWINGS

These and other aspects will now be described in detail with reference to the accompanying drawings. Like reference symbols in the various drawings indicate like elements.

FIG. 3A shows a representation of a needle assembly within the needle assembly housing and in conjunction with an introducer.

FIG. 3B shows representative parts of a needle assembly of FIG. 3A in expanded view.

FIG. 4 shows a planar and cut-away view of a needle system of the invention.

DETAILED DESCRIPTION OF THE INVENTION

The invention relates to over the needle catheter and peel away introducer assemblies including a safety needle assembly that prevents disconnection of the safety needle assembly from a catheter or introducer until the needle is safely housed within the safety needle assembly in a "needle safe position".

The invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain embodiments of the invention. Furthermore, embodiments of the invention may include several novel features, no single one of which is solely responsible for its desirable attributes or which is essential to practicing the inventions herein described.

Figure 1:
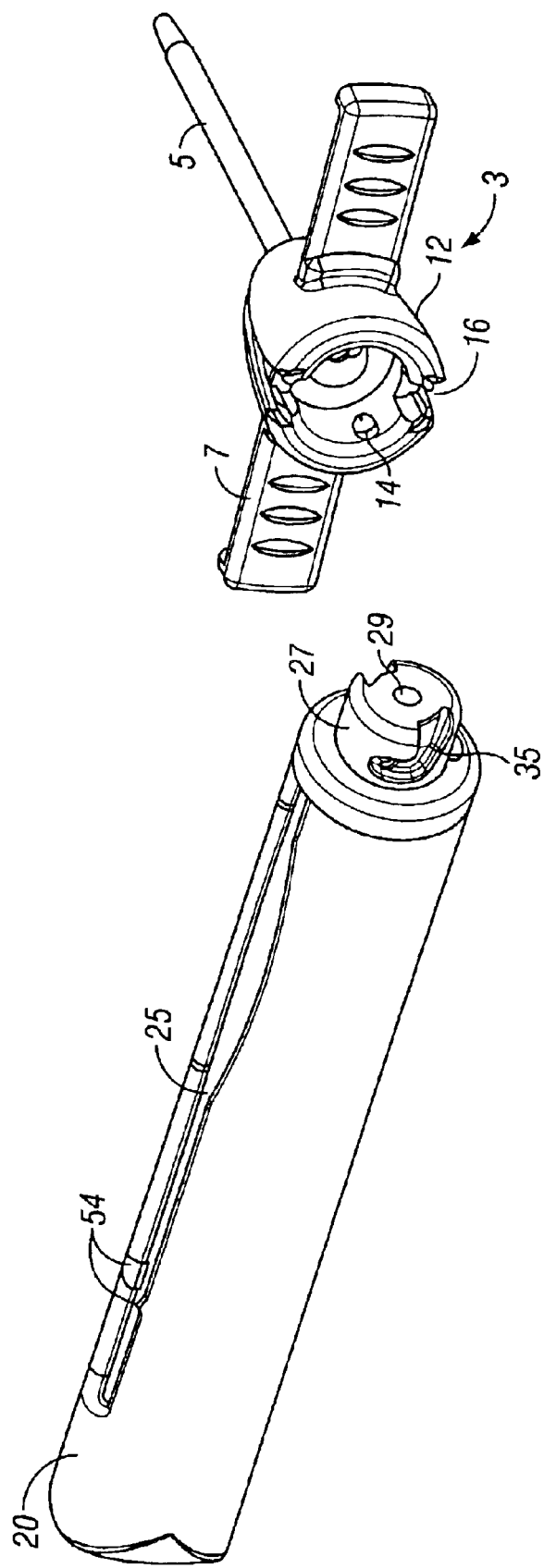
FIG. 1 shows a schematic of an introducer and a housing for a needle assembly of the invention.

FIG. 1 depicts an introducer that may be used in conjunction with the needle assembly of the invention. In FIG. 1 there is shown an introducer 3 comprising one or more flanges 7, which may be variably located on the introducer. Hollow needle 5 is connected to connector bowl 12 comprising a sealable septum 30 (see, e.g., FIG. 2), one or more locking notches 16, and threads or one or more attachment detent 14. In use hollow needle 5 (e.g., a tubular structure such as a cannula, catheter, introducer, trocar, a blunt or sharp hollow needle, and the like) is inserted in to a subject's vein or other organ to facilitate introduction of a device, the aspiration of a fluid or tissue, and/or the infusion of a fluid. Septum 30 prevents fluids from flowing through the hollow needle 5 and out connector bowl 12. Flanges 7 assist a user in removal and/or separation of the introducer from a second introduced device (e.g., a catheter). Hollow needle 5 is fluidly connected to connector bowl 12.

Also shown in FIG. 1 is needle assembly housing 20. The housing 20 is shown as being substantially cylindrical although other shaped housings can also be used (e.g., rectangular). Also shown are threads 35 to receive thread or detents 14 on introducer 3, needle opening 29, and male portion 27, which is received by connector bowl 12. Slot 25 is also shown in housing 20 and allows sliding of needle handle 42 (see below).

FIG. 1 also shows introducer 3 in juxtaposition with needle assembly housing 20. A locking tab 22 (see FIG. 2) is located on an exterior part of the housing, attached to an internal slide mechanism 48 (discussed below). This locking tab presses against the connector bowl 12 and locks the needle housing 20 relative to the connector bowl 12. For example, when an introducer 3 is connected to housing 20 the needle housing 20 is attached to the introducer by threaded fixture part/detent 14 and threads 35. The locking tab 22 then interacts with locking notch 16 thereby preventing rotation of the needle housing relative to the introducer thus locking the housing to the introducer. An internal needle (see below) is movable through opening 29 in housing 20 during connection to, for example, introducer 3.

Figure 2:
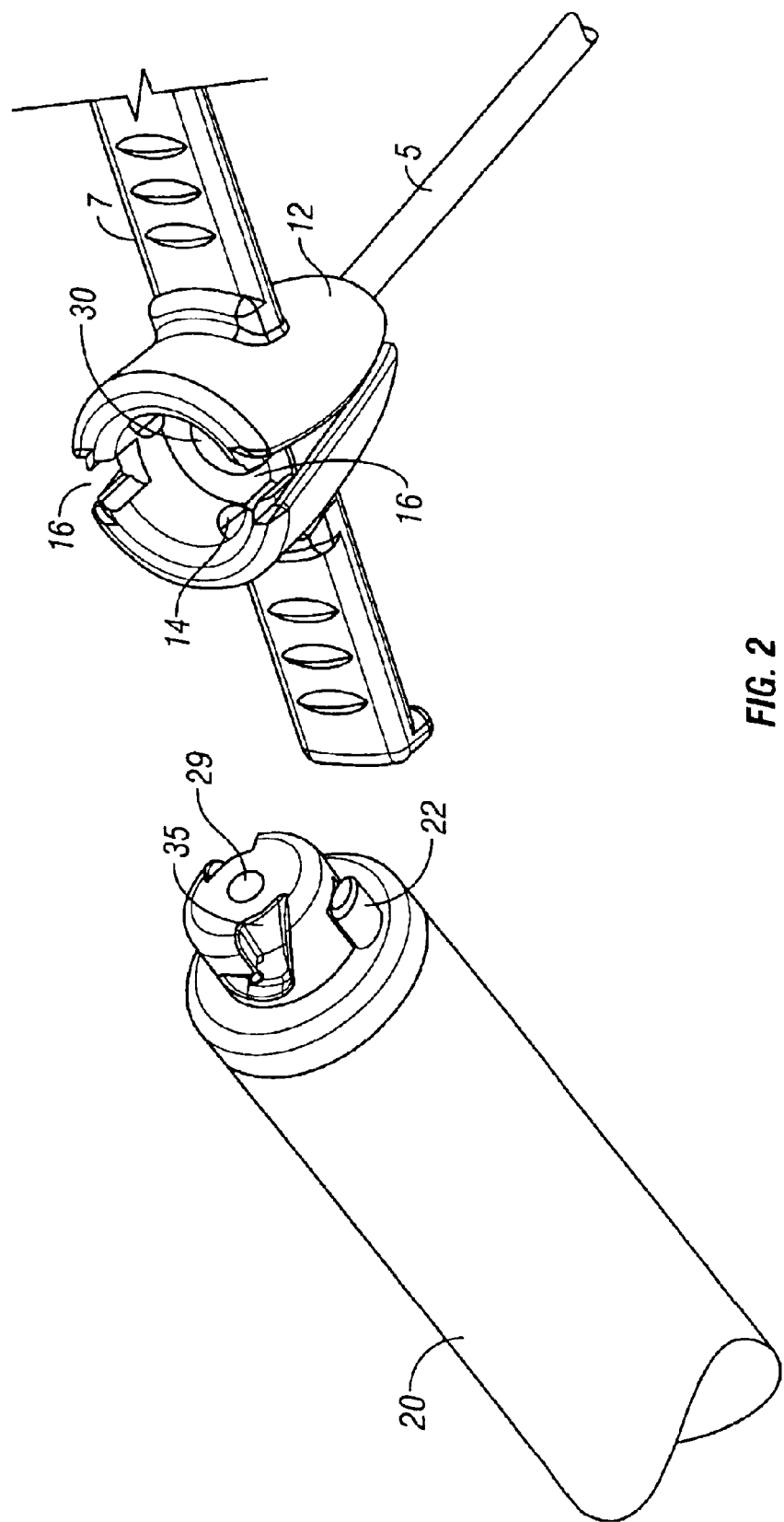
FIG. 2 shows a magnified view of needle housing and an introducer.

FIG. 2 shows an enlarged view of introducer 3 in juxtaposition with needle assembly housing 20. A locking tab 22 is depicted in FIG. 2, which is attached to an internal slide mechanism (discussed below). Introducer 3 comprises hollow needle 5 connected to connector bowl 12 comprising a sealable septum 30, one or more locking notches 16, and threads or one or more attachment detent 14. Upon connection of housing 20 to introducer 3, male portion 27 is received by connector bowl 12 such that opening 29 is adjacent to or in contact with septum 30 and wherein opening 29 is in alignment with hollow needle 5. In addition, upon connection of housing 20, threads 35 receive introducer thread/detent 14 and upon twisting the locking tab 22 will align with locking notch 16. When locking tab 22 is aligned and engaged with locking notch 16, the engagement prevents dissociation or disconnection of housing 20 from introducer 3. Similar conceptual alignments and associations can be made with catheter devices comprising variations on connector bowl 12.

In yet a further aspect of the invention the locking tab and locking notch can be used to physically secure the two parts (e.g., the connector bowl and housing) together when threads are not required or present.

FIG. 3A shows needle assembly device 2 comprising housing 20, a needle handle 42, flanges 7, connector bowl 12, hollow needle 5, and an internal needle 40. With reference now to FIG. 3B, the housing has internal surfaces 55 defining a first sliding area. An internal slide mechanism 48 (shown in further detail in FIG. 5) is located within the inner surfaces 55. The outer surfaces 48a of the internal slide mechanism 48 aligns and fits within and slides against the internal surfaces 55 as explained herein. The slide mechanism 48 also includes internal surfaces 48b, which define a second sliding surface. The inner surfaces 48b receive a needle handle 42 and/or internal handle portions 44 both of which are operatively connected to an internal needle 40 comprising a pointed needle of any type. The needle handle 42 and internal handle portion 44 can be moved within the surfaces 55 to change the position of the internal needle 40 as explained herein. The internal handle portion 44 also defines a flashback chamber, which includes a porous plug 46. A locking tab 22 projects through the male portion 27 and is attached to the internal slide mechanism 48. This locking tab presses against the connected part (e.g., introducer 3) and locks the needle housing 20 relative to the connected part (e.g., introducer 3). For example, when the connected part is an introducer, the needle is locked to the introducer by interaction of a locking tab 22, with locking notch 16. As mentioned above, a threaded fixture part 35 is provided facilitating the attachment to an introducer if necessary.

In this embodiment, a double sliding mechanism is used. The needle handle 42 itself may slide within slot 25 and the internal slide area defined within the inner surfaces 55. Alternatively, the needle handle 42 may slide on the internal surface 48b of the internal slide mechanism 48. The internal slide mechanism 48 moves within the housing 20. In one aspect of operation, a first sliding action is necessary before the second sliding action can take place. The first sliding action brings the internal needle 40 further within the housing 20. During this first sliding action handle 42 is moved such that the internal handle portion 44 or a part thereof (e.g., 44a) interacts with internal slide mechanism flanges 50. Upon contact of the internal handle portion 44 or part 44a with internal sliding mechanism flanges 50, a second sliding action is begun. The second sliding action results in the sliding of internal slide mechanism 48 within housing 20. The sliding of mechanism 48 results in the sliding of locking tab 22 (attached to mechanism 48). Locking tab 22 is thus removed from locking notch 16 (see, e.g., FIGS. 1 and 2), thereby enabling disconnection from the introducer. The locking tab 22 is fully withdrawn from locking notch 16, when internal needle 40 is fully withdrawn into housing 20. Therefore, this system prevents disconnection from the introducer until the internal needle 40 is in a needle safe position.

In operation, the internal needle 40 can be inserted into an introducer 3. Prior to the insertion process, the internal needle is clean and therefore no danger occurs. During insertion, needle handle 42 is in a forward position. As the needle system 2 is pressed forward, the needle penetrates a patient's organ (e.g., skin) facilitating the insertion of the hollow needle 5. Internal needle 40 thereby comes into contact with contaminants comprising biological tissue and the like. To remove the internal needle 40 from the introducer 3 the needle handle 42 is slid backwards within the internal surface of the housing 20, thereby pulling the needle handle 42 in to contact with the inner slide mechanism 48.

FIG. 4 shows the needle handle 42 having been pulled towards a needle safe position. This correspondingly causes the internal needle 40 to also be pulled back. As shown, the part of the internal needle 40 which is extended through tip of hollow needle 5 in FIG. 3A is well within the housing 20 and is not present in hollow needle 5, or connector bowl 12 of the introducer 3. As the needle handle 42 is moved back, the handle 42 and/or internal handle portion 44 reaches the rear most area within of the internal slide mechanism 48. At this position, the needle handle 42 and/or internal handle portion 44 interact with the rear most area of the internal slide mechanism 48 comprising flanges 50. As a user continues to provide mechanical pressure against the needle handle 42, this causes the internal slide mechanism 48 to move within the housing 20 and slide the internal slide mechanism 48 back away from the end comprising hollow needle 5. Accordingly, in addition to the internal needle 40 moving, the internal slide mechanism 48 has also been engaged and has been slid back from away from the hollow needle 5 and connector bowl 12 into the housing 20. As part of internal slide mechanism 48 moving, locking tab 22 also moves out of locking notch 16. The movement of internal slide mechanism 48 within the housing 20 releases the locking tab 22, and thereby unlocks the needle assembly housing 20 from the introducer 3 to allow its safe removal. Note that the unlocking cannot occur until the needle is totally withdrawn into the housing 20. The locking mechanism prevents the operator from removing the needle until there is absolute certainty that the needle is in its safe position within the housing.

FIG. 5 shows a cut-away of a needle assembly of the invention. FIG. 5A shows internal slide mechanism 48 in more detail. Internal slide mechanism 48 comprises a locking tab 22; an outer sliding surface 48a; an inner sliding surface 48b within which the handle/needle assembly also slides; internal slide mechanism flanges 50; and slide mechanism tongue 60. The slide mechanism tongue 60 provides resistive force preventing slide mechanism 48 from sliding backward accidentally and thereby inadvertently releasing locking tab 22 from its engagement with locking notch 16.

Figure 5A:
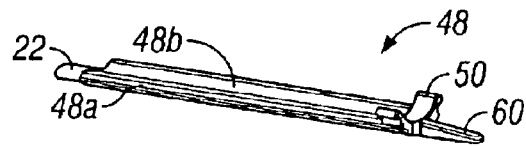
FIG. 5 collectively shows a number of cut-aways of a needle assembly of the invention.
Figure 5B:
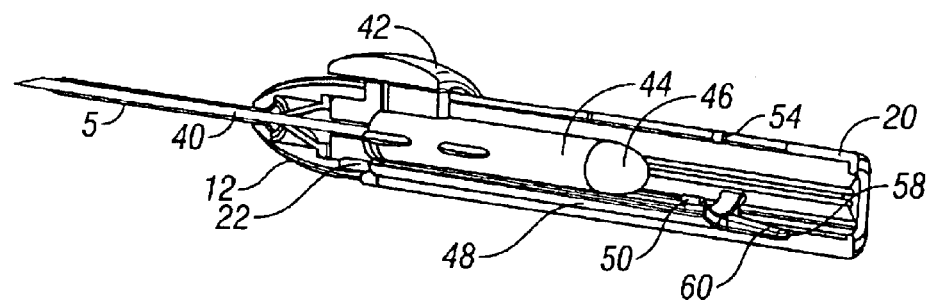

FIG. 5B shows a cut-away of the needle assembly connected to an introducer. Here needle handle 42 is fully forward resulting in internal needle 40 being fully extended through hollow needle 5 of introducer 3. In this position, locking tab 22 is extended into connector bowl 12 thereby preventing rotation of the bowl during unscrewing of the bowl 12 from the needle housing 20. In one aspect of the invention, a spring or forward flange of the internal slide mechanism 48 maintains the internal slide mechanism 48 in a forward position thereby maintaining the locking of the housing 20 with introducer 3. In one aspect, the slide mechanism tongue 60 provides resistance against resistance ledge detent 58 of housing 20 to prevent inadvertent movement.

Figure 5C:
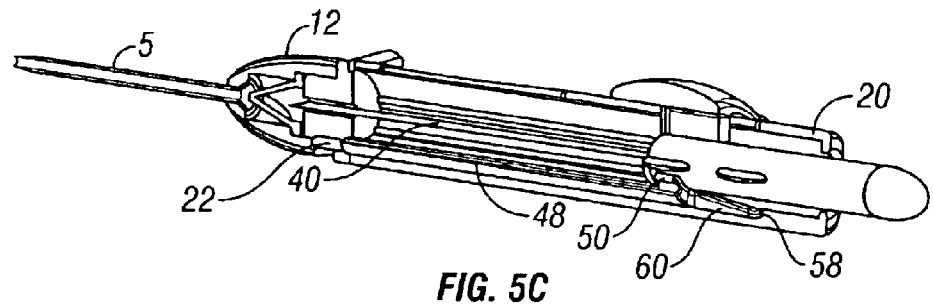

FIG. 5C shows the needle handle 42 having been pulled approximately three-fourths of the way back within the housing 20. This correspondingly causes the internal needle 40 to also be pulled back. As shown, only the very tip of the internal needle 40 extends beyond the housing 20 into the area of the bowl 12. Importantly, during this time, however, the internal slide mechanism 48 has not moved within the housing 20. As the needle continues to move back, eventually the needle handle 42 reaches the rear most area of the internal slide mechanism 48. At a point during the sliding of the needle handle 42, the needle handle 42 and/or an internal needle handle portion 44a comes into contact with rear internal slide mechanism flanges 50. Upon contact, sliding will become more difficult as resistance is imposed by contact of internal sliding mechanism tongue 60 with resistance ledge detent 58.

Figure 5D:
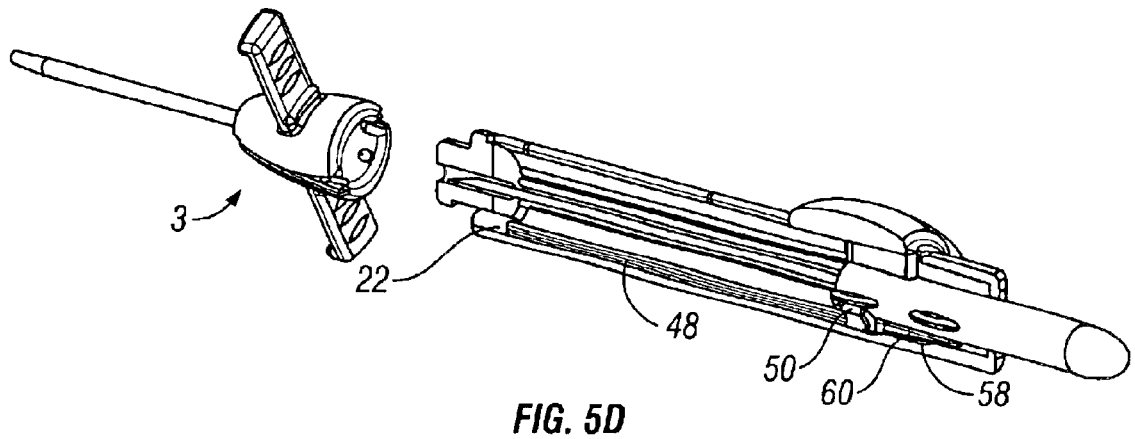

FIG. 5D shows the introducer 3 removed from the housing 20. The removal of the introducer 3 can only be performed once the internal needle 40 is safely housed and the locking tab 22 is slid back and out of locking notch 16. In FIG. 5D internal sliding mechanism flanges 50 have been engaged by handle 42 and/or handle portion 44a. The needle handle 42 is further slid back to overcome the resistance imposed by tongue 60 and resistance ledge detent 58. As the tongue 60 slides up and over resistance ledge detent 58, the needle handle 42 is locked into place by detents 54 (see FIG. 1) within the housing 20 to prevent the internal needle 40 from accidentally sliding back forward. In addition, locking tab 22 has been slide back from locking notch 16. The internal needle 40 is fully within housing 20 at this position, a needle safe position.

Figure 6A:
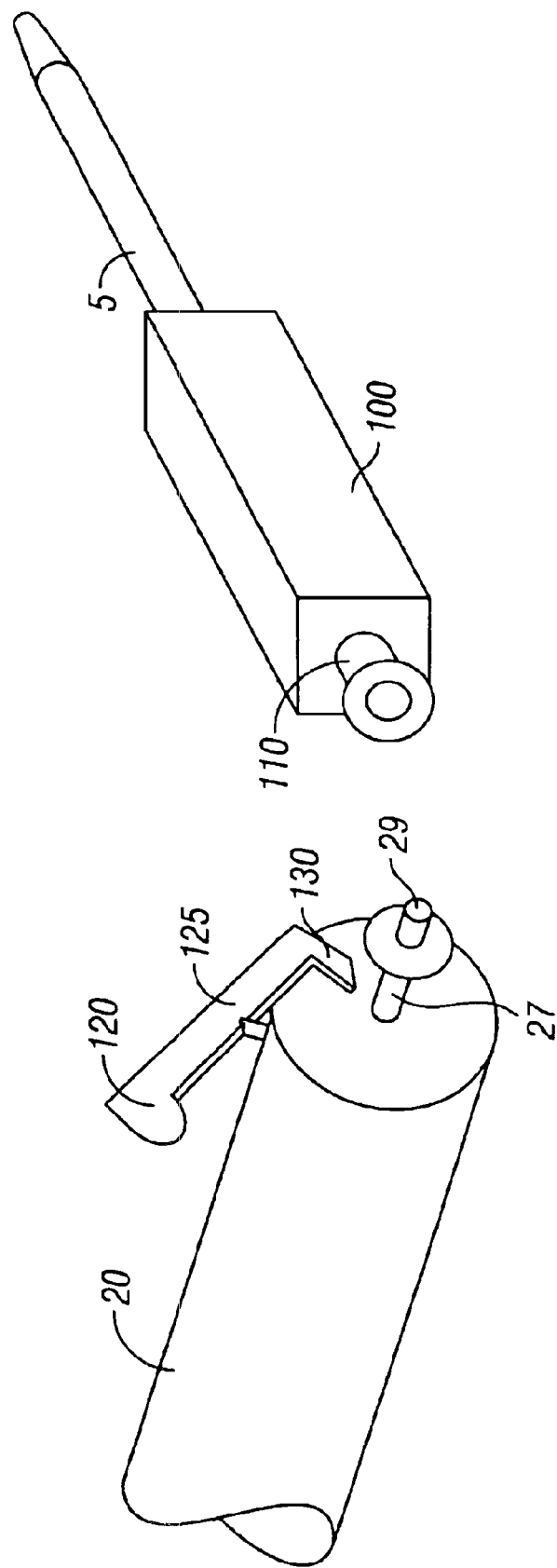
FIGS. 6A–C show a frictional engagement locking system of the invention.
Figure 6B:
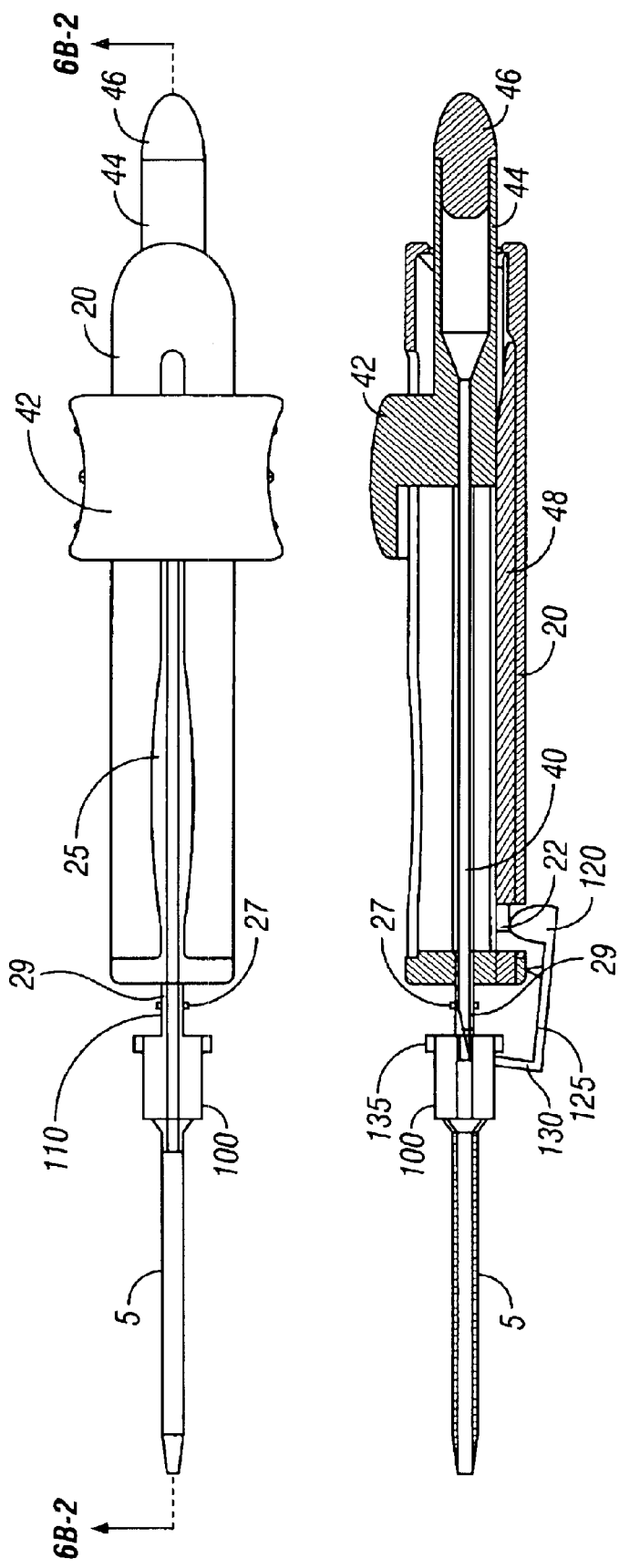

In one aspect the invention provides a frictional engagement locking system. With reference to FIGS. 6A and 6B, there is shown an embodiment depicting a frictional aspect of the invention. In this aspect, a catheter device 100 utilizes a female luer connection 110 to connect to the needle assembly. For such catheter devices male portion 27 will create a frictional engagement with female luer connection 110. Threading may actually occur on the outside surface of the female luer connection 110 rather than the internal threading described above. In this aspect, a biased hammer device 125 is located on the outside of housing 20 such that an engagement end 130 of hammer device 125 interrupts the thread pattern and prevents disconnection until safety conditions are met.

FIG. 6B shows in further detail a locking mechanism used in a frictional engagement locking system. During operation catheter device 100 is connected to male portion 29 of housing 20. As needle handle 42 is slid forward towards the catheter device, internal sliding mechanism 48 contacts and raises hammer end 120 of hammer device 125 thereby pivoting the hammer device resulting in engagement of engagement end 130 with catheter device 100. Upon engagement of end 130 with catheter device 100 rotation of the catheter device 100 is prevented. In another aspect, where there are no threads present on the connection device (e.g., needle, cannula, or catheter) the catheter device may comprise ledge 135 which would prevent removal of the catheter until engagement end 130 is raised. The catheter device 100 can be removed when engagement end 130 is pivotally disengaged from the catheter device 100 by pulling the needle handle 42 aft. As the needle handle 42 is pulled aft, internal sliding mechanism 48 is also pulled aft thereby lowering the hammer end 120 and pivotally raising engagement end 130. Once the handle is fully aft the catheter device may be disengaged.

Figure 6C:
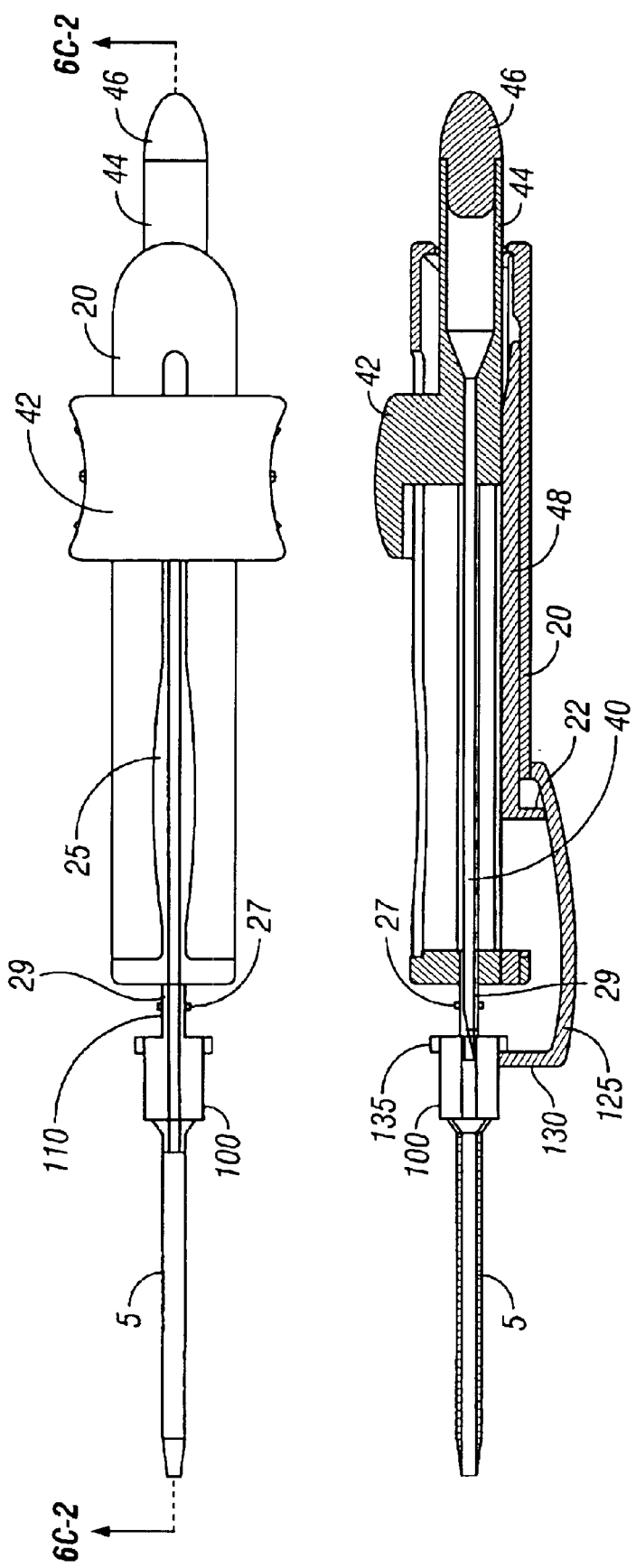

FIG. 6C shows in further detail an alternate embodiment of a locking mechanism used in a frictional engagement locking system. During operation catheter device 100 is connected to male portion 29 of housing 20. Locking arm 125 is connected to or an integrally molded part of housing 20 such that in its resting position end 130 is biased toward internal needle 40. As needle handle 42 is slid forward towards the catheter device, internal sliding mechanism 48 is not in contact or in minimal contact with locking arm 125. When internal sliding mechanism 48 is forward the end 130 is engaged with catheter device 100 to lock it into position. Upon engagement of end 130 with catheter device 100 rotation or removal of the catheter device 100 is prevented. In another aspect, where there are no threads present on the connection device (e.g., needle, cannula, or catheter) the catheter device may comprise ledge 135 which would prevent removal of the catheter until engagement end 130 is raised. The catheter device 100 can be removed when engagement end 130 is pivotally disengaged from the catheter device 100 by pulling the needle handle 42 aft. As the needle handle 42 is pulled aft, internal sliding mechanism 48 is also pulled aft thereby engaging the aft end of locking arm 125 and raising the hammer end 130. Once the handle is fully aft the catheter device may be disengaged.

The devices described herein may be formed of a number of separable parts, which may be sold and packaged as a unit, or may be separable so that they can be separately manufactured, sterilized, and sold. For example, the introducer comprising the hollow needle 5; the needle handle 42 comprising internal handle portion 44 and internal needle 40; and housing 20, may each be sold and/or packaged separately and may also be sterilized separately.

In certain aspects of the invention internal needle 40 comprises a stainless steel material. Typically the internal needle 40 will be rigidly coupled to the needle handle 42. The needle handle 42 may be a translucent handle with a flashback chamber that allows viewing of blood flow or fluid flow and hence determining if the device has been properly inserted. The plug 46 may comprise a porous plug, resealable septum, rubber stopper, or a small needle assembly for connection of vacutainer tubes for collection of biological specimens. Of course, the actual needle/handle assembly 2 may have a different overall shape. The internal needle 40 should be securely attached to the needle handle 42 and internal handle portion 44, which has a pressing surface 52 (see FIG. 3). The handle should also have substantially symmetrical pressing parts so that either a right or left-handed person can easily use it. Ideally, the handle shape should be one that can be relatively easily grasped using the thumb and forefinger.

The internal slide mechanism 48 comprises a locking mechanism (e.g., tongue 60) to lock the internal slide mechanism 48 as described above at a fully forward position (comprising engagement of locking tab 22 with notch 16). When needle handle 42 is in the fully retracted position, the internal needle 40 is safely housed, internal slide mechanism 48 and locking tab 22 are fully retracted, and the needle handle 42 is locked into position by detents 54 (see FIGS. 1 and 5). Locking of needle handle 42 by detents 54 prevents needle handle 42, internal needle 40, internal slide mechanism 48, and locking tab 22 from moving forward. The locking mechanism for the needle safe position may take the form of a special detent or ledge in combination with a needle handle as explained herein. Locking could also be accomplished by securing the needle handle to a locked position to internal slide mechanism 48 and then utilizing detents to hold internal slide mechanism 48 from moving forward. The handle should also have a female type connector for connecting to the porous plug and/or syringe.

The internal slide mechanism 48 may take any shape. The preferred mode may use flat surfaces as shown to facilitate the formation, although any shape surfaces may be used.

The device described above was described in combination with an introducer or catheter. A further embodiment provides use of the needle assembly with a catheter that has a female luer. Catheters typically terminate in a female luer. In this assembly, the locking tab presses against a specified portion, to interrupt the thread pattern of the catheter's female luer. In this aspect, the locking tab 22 enters the thread pattern of the luer and prevents rotation of the needle assembly while engaged with the luer. Rotation is thereby prevented until the tab is retracted, thereby preventing the needle from being removed until absolute safety is established.

While the above has described this specific case of the screw connection for an introducer, a connection for a catheter can also be similarly used. In general, for any device that attaches by rotating, the tab can simply stop for the rotation.

Although only a few embodiments have been disclosed in detail above, other modifications are possible. All such modifications are intended to be within the scope of the following claims. As is also stated above, it should be noted that the use of particular terminology when describing certain features or aspects of the invention should not be taken to imply that the terminology is being re-defined herein to be restricted to include a specific characteristic, feature, or aspect of the invention with which that terminology is associated. The scope of the invention should therefore be construed in accordance with the appended claims and any equivalents thereof.

What is claimed is:

1. A safety needle assembly, comprising:

a housing a needle assembly within said housing, which is movable between an extended position, and a retracted position;

a locking assembly, which locks said needle assembly in said retracted position;

a needle locking mechanism, which locks said housing to a connected device;

a mechanical movement assembly which allows another movement only when said needle assembly is in said retracted position, said another movement being one which enables removing said needle assembly from the connected device wherein said another movement comprises retraction of another device relative to said housing.

2. An assembly as in claim 1, wherein said needle assembly is movable between said extended position in which a needle of the needle assembly extends outside said housing, and said retracted position in which the needle retracts inside the inner surfaces defining said housing.

3. An assembly as in claim 1, wherein said mechanical movement assembly comprises a slide assembly, and said retraction relative to said housing comprises sliding said slide assembly against inner surfaces of said housing.

4. An assembly as in claim 3, further comprising a connection between said slide assembly and said needle locking mechanism.

5. An assembly as in claim 4, wherein said connection enables said needle locking mechanism to be removed from said connection once said slide assembly is in a specified position.

6. An assembly as in claim 1, wherein said housing is substantially cylindrical in shape.

7. An assembly as in claim 1, wherein said needle assembly includes a handle part, with a part for pressing said needle assembly.

8. An assembly as in claim 7, wherein said handle part is substantially clear.

9. An assembly as in claim 7, wherein said handle part includes a part enabling detection of blood flow.

* * * * *